United States Patent
Jones

(10) Patent No.: US 10,682,261 B2
(45) Date of Patent: Jun. 16, 2020

(54) BREATHABLE INSTANT CAST

(71) Applicant: Joseph S. Jones, OT (IT)

(72) Inventor: Joseph S. Jones, OT (IT)

(*) Notice: Subject to any disclaimer, the term of this patent is extended or adjusted under 35 U.S.C. 154(b) by 640 days.

(21) Appl. No.: 15/289,623

(22) Filed: Oct. 10, 2016

(65) Prior Publication Data
US 2017/0020738 A1    Jan. 26, 2017

Related U.S. Application Data

(63) Continuation-in-part of application No. PCT/US2015/025332, filed on Apr. 13, 2015.

(60) Provisional application No. 61/978,619, filed on Apr. 11, 2014.

(51) Int. Cl.
| | | |
|---|---|---|
| A61F 5/00 | (2006.01) | |
| A61F 13/04 | (2006.01) | |
| A61F 5/01 | (2006.01) | |
| A61F 13/00 | (2006.01) | |

(52) U.S. Cl.
CPC .............. *A61F 13/046* (2013.01); *A61F 5/01* (2013.01); *A61F 13/04* (2013.01); *A61F 2013/00489* (2013.01); *A61F 2013/00548* (2013.01); *A61F 2013/00608* (2013.01); *A61F 2013/00621* (2013.01); *A61F 2013/00855* (2013.01)

(58) Field of Classification Search
CPC ...... A61F 13/04; A61F 13/041; A61F 13/046; A61F 13/048
See application file for complete search history.

(56) References Cited

U.S. PATENT DOCUMENTS

| | | | | |
|---|---|---|---|---|
| 4,294,240 A | * | 10/1981 | Thill | A61F 13/041 602/21 |
| 4,793,330 A | * | 12/1988 | Honeycutt | A61F 13/04 523/105 |
| 5,415,622 A | * | 5/1995 | Kelley | A61F 13/04 602/5 |
| 5,916,184 A | * | 6/1999 | McKeel | A61F 13/04 428/71 |
| 6,585,671 B2 | * | 7/2003 | Rhee | A61F 13/04 602/5 |
| 6,613,006 B1 | * | 9/2003 | Asherman | A61F 13/04 602/20 |
| 6,673,029 B1 | | 1/2004 | Watson | |
| 7,314,457 B2 | * | 1/2008 | Reaux | A61F 13/04 602/6 |
| 7,465,283 B2 | * | 12/2008 | Grim | A61F 5/01 602/5 |
| 2003/0093025 A1 | | 5/2003 | Rhee | |

(Continued)

OTHER PUBLICATIONS

International Search Report and Written Opinion in corresponding International Application No. PCT/US2015/025332 dated Jun. 29, 2015.

*Primary Examiner* — Kim M Lewis
(74) *Attorney, Agent, or Firm* — Bond, Schoeneck & King, PLLC; Joseph Noto

(57) ABSTRACT

An instant breathable cast includes an inner sleeve of an absorbent moisture wicking porous innermost layer allowing air and liquid to pass through and a shock absorbing intermediate layer having a plurality of openings therein allowing air and liquid to pass there through; and a protective outer sleeve having a plurality of openings therein allowing air and liquid to pass there through; and method of application thereof.

19 Claims, 7 Drawing Sheets

(56) References Cited

U.S. PATENT DOCUMENTS

2006/0155226 A1 7/2006 Grim
2015/0208736 A1* 7/2015 Bergman ............... A41D 13/08
 2/69
2015/0305914 A1* 10/2015 Wu .......................... A61F 5/01
 602/7

* cited by examiner

BREATHABLE INSTANT CAST

CROSS REFERENCE

This application claims the benefit of the filing date of U.S. Provisional Patent Application Ser. No. 61/978,619, filed Apr. 11, 2014 and International Application No. PCT/US2015/025332, filed Apr. 10, 2015, which is hereby incorporated by reference in its entirety.

FIELD

The present disclosure relates to a cast and method for application thereof, and in particular to a breathable instant cast.

BACKGROUND

When humans or animals sustain displaced fractures of their long bones, they often have to undergo reduction of the fracture followed by placement of a fiberglass or plaster cast. Casting often involves immobilization of the arm or leg for 6 weeks. The application of a cast is typically a four part process: 1) placement of the stockingette; 2) overwrapping the limb with a thin cotton under cast padding material that provides padding between the limb and the cast; 3) applying the casting material itself; and 4) placing a 3 point mold in the cast which will hold the fracture in a reduced position. During step 2 and step 3 there are numerous mistakes that can be made which will not only lead to a lost fracture reduction over time, but will also subject the patient to a skin injury from an over packed or under protected pressure point. For example, the casting material is typically provided as a roll of a strip of soft material that must be wrapped around the limb in successive applications as it dries and hardens due to exposure to the air. In the United States, acute casting of a long bone fracture is often performed by orthopedic surgeons, orthopedically trained Physicians assistants or Nurse practitioners. Cast technicians usually assist with placement of large casts or apply casts to bones that are partially healing and do not require reduction.

During the time that the casts are being worn, the patient has to keep the inside of the cast dry. Traditional casts trap water between skin and cast. In the case of plaster casts, they must keep the outside of the cast dry as well. For small children in the summer time this could mean missing out on water activities. For the adolescent athlete or adult, this often means choosing between aerobic exercise and a relatively dry, less smelly and itchy cast. Keeping casts dry, clean, and intact may be difficult in austere environments or in developing countries with limited medical care or shelter for patients between appointments. Cast removal requires a cast saw which is loud, tends to scare children, and can subject patients to skin injuries if it is not used properly.

Currently there are several remedies for each of these challenges, but there are no products which address all of these issues simultaneously. One product is a GORE-TEX® padding (aqua cast) which can be applied usually around week 3 post-injury when the original cast is changed out. This however, has the objective of keeping water away from the skin. It can sometimes lead to small amounts of trapped moisture that macerate the skin. Another product is the EXOS® fracture brace which is not intended for holding reduced fractures in place and is only available in the short arm format. This product is aimed at treatment of non-displaced fractures, or fractures that have partially healed. This product also requires an oven made by the company that makes EXOS® for the purpose of heating the device so that it can be molded to the patient after it has been tightened down.

The art lacks a device to provide patients and healthcare professionals with a solution that can be applied immediately after injury, with minimal expertise, that allows the patient to perform routine hygiene without removing the cast or splint, and allows for removal of the cast without the use of a saw.

SUMMARY

In accordance with one aspect of the present disclosure, there is provided an instant breathable cast including an innermost layer having an absorbent moisture wicking porous material which allows air and water to pass there through; an intermediate layer including a shock absorbing material having a plurality of openings therein which allow air and water to pass there through; and a pliable outermost layer including a protective material having a plurality of openings therein which allow air and water to pass there through.

In accordance with another aspect of the present disclosure, there is provided a method for applying a cast to a patient including applying an innermost layer over a limb by sliding a sleeve of innermost layer material over the limb, wherein the innermost layer is composed of a porous material; applying an intermediate layer over the limb by sliding a sleeve of intermediate layer material over the limb, wherein the intermediate layer is composed of a porous foam material; applying, while still in packaging, an outermost sleeve in the form of a flexible tube into place over the limb; removing the packaging from the outermost sleeve; exposing the outermost sleeve to water and air; and fitting the cast to the patient while allowing the cast to air dry during the fitting thereof.

These and other aspects of the present disclosure will become apparent upon a review of the following detailed description and the claims appended thereto.

DETAILED DESCRIPTION

Figure 1:
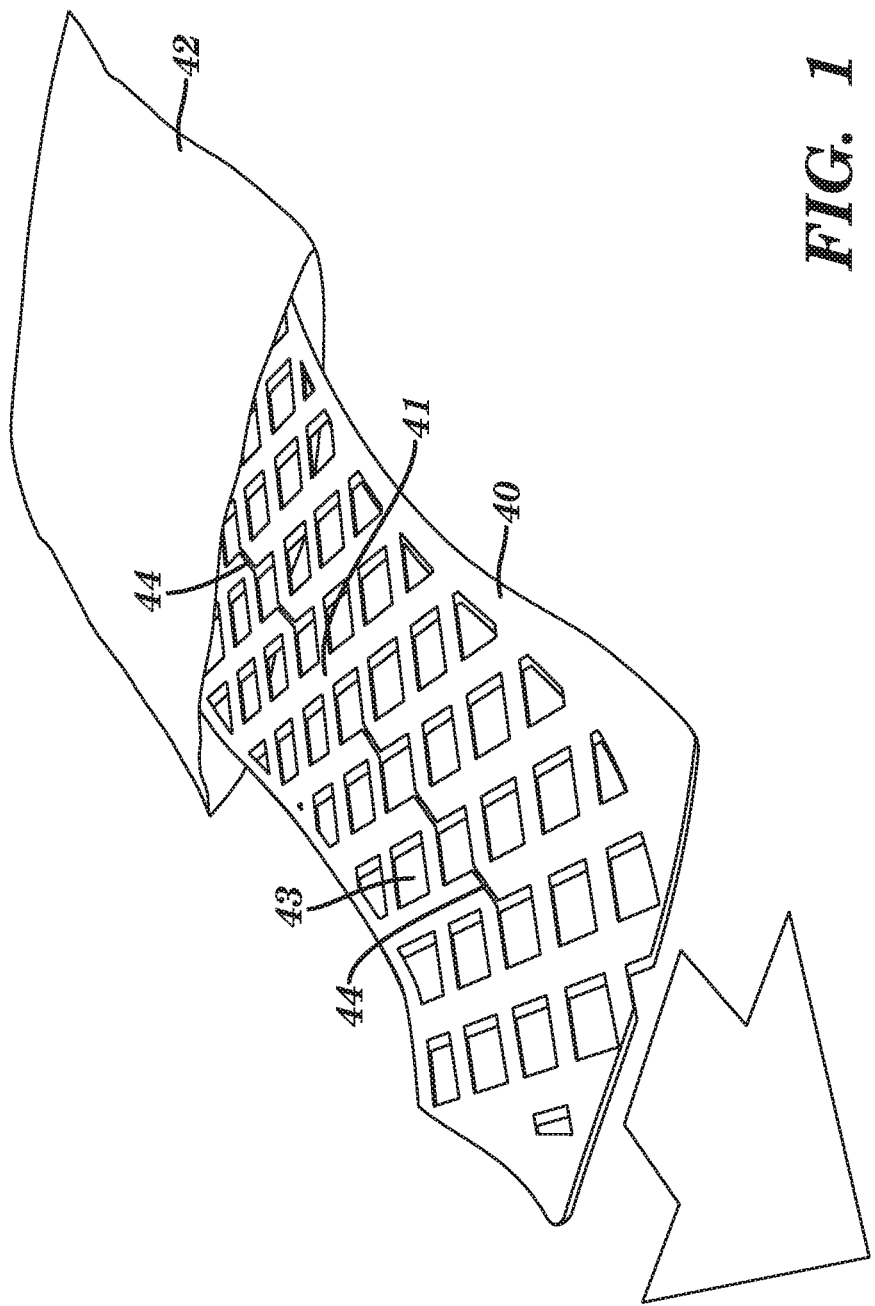
FIG. 1 is a drawing of an embodiment of the outer sleeve of the cast of the present disclosure.

The present disclosure relates to a breathable instant cast and method of application to a patient, aimed at creating a quick and easy solution to bone fractures which reduces the expertise required for application, and allows for simple hygiene without removal of the cast. The casting of the present disclosure is considered instant when compared to known methods of casting a broken limb, which typically requires each layer to be independently constructed and carefully applied in a process that takes about 15-20 minutes to do correctly and is often unforgiving and mistake prone. The cast of the present disclosure can also be utilized by military personnel or people operating in austere environments without access to adequate medical care. The present disclosure will be able to do all of this while fitting the patient perfectly, and causing no harm via pressure points from over/under padding or cast indentations.

The present disclosure is described herein by reference to an embodiment of a short arm cast for simplicity purposes, but the disclosure is not so limited and includes, for example, all types of casts on both the upper and lower extremities, such as for example, long arm, short arm, short leg, long leg, dorsal hood, hip spica casts, and the like, and variations of these casts. The disclosure also relates to casts that are adaptable to animals requiring long bone fracture reduction and stabilization.

The device achieves these objectives by being manufactured in different sizes for children and adults and preferably includes pre-formed components. The sizing for example is analogous to the range and distribution of shoe sizes, and could be based on patient height, long bone length, or both, as desired.

In an embodiment of the disclosure, the cast is composed of an inner sleeve and an outer sleeve. In an embodiment, the cast is composed of three layers, but may be composed of other numbers of layers or designs. In an embodiment, the cast includes an innermost layer, intermediate layer, and outermost layer. Preferably, certain or all layers can be attached to each other, for example, layers that have been essentially woven, sewn, or glued together prior to packaging.

In an embodiment, the innermost layer is composed of a super absorbent, moisture wicking material that is porous, such as Dri-Release®. Optionally, the innermost layer can have holes in it to allow for the free exchange of air and fluid between the skin surface and the outer surface of the outermost layer, as for example, having 1 cm holes throughout the length of the material of the innermost layer. Other designs that allow for the free exchange of air and liquid between the skin surface and the outer surface of the outermost layer are suitable.

In an embodiment, the intermediate layer is composed of a sleeve of shock-absorbing material. The intermediate layer is suitably made of a soft material, such as packing foam, neoprene, or a porous rubber. The intermediate layer functions as a cushioning layer. For example, the intermediate layer can be approximately ½ to 1 cm in thickness. Other designs that allow for the free exchange of air and liquid and provide cushioning are suitable.

In an embodiment, the outermost layer is a protective layer. Suitable materials for the outermost layer include fiberglass. In an embodiment, the fiberglass layer of the present disclosure does not come as a roll of a single layer of material that is wound around or layered over a limb, but rather can be manufactured as a glove-like sleeve that can be slid into place and then trimmed if necessary. For example, the fiberglass layer can be in the form of a patterned flexible tube that is slid into place over the extremity. The outermost sleeve is made of soft pliable casting material that is protected by packaging material until it is ready to be used. The outer protective layer has a longitudinal slit or a plurality of longitudinal slits from one end to the other end. Other designs that allow for the free exchange of air and liquid and provide protection are suitable.

The outermost component is a protective lattice patterned sleeve which can be made of suitable casting material, such as fiberglass, for example, knitted fiberglass fabric impregnated with water/air activated resin, for example, polyurethane. Since initially, the fiberglass reacts with both water and air, the outermost component is preferably manufactured and sealed from the atmosphere until it is in place and ready to be dipped in water upon which it hardens. This protective sleeve is sized in accordance with the manner of the first two layers. It can be pulled into place while still in the packaging to ensure that the correct size is being used. Then once the package is stripped off from around it, it can be trimmed, if necessary.

In an embodiment, the outermost lattice pattern layer is a casting material that is manufactured as a single pliable long sleeve that can be provided in a roll form. When applying to a patient, the health care provider cuts a length about 3 to 4 times the length of the patient's limb. The sleeve is then folded back over itself about 3 to 4 times to generate a cast that is about 4 to 5 layers think. Once hardened, a cast is created that is strong enough to hold a bone in place, while allowing air and moisture to pass freely. In the field, if warranted the folded-over sleeve can be applied directly to the injured limb without any inner or intermediate layers. The single long sleeve can be manufactured into the desired lattice shape, for example, by use of a netting machine or cargo net knitting machine to make a sleeve in the dimensions and specifications optimal for a breathable cast. The outermost layer sleeve can be fabricated as a cylindrical lattice-patterned cage made of knitted fiberglass fabric impregnated with a water/air activated resin. The outermost layer sleeve can be fabricated as a net made of knitted fiberglass fabric impregnated with a water/air activated resin.

In an embodiment, the outermost layer is reinforced with one or more rings of material to provide added strength. Initially, a single layer sleeve cast is provided with a solid ring on each end for added stability. For example, the lattice pattern of a forearm sleeve terminates about 10 centimeters from the edge of the cast at the top, bottom, and around the thumb portion. In a further embodiment, an added second outer layer composed of multiple spaced apart rings takes advantage of the strength provided from the adherence between two adjacent layers while promoting adequate air and water flow. The rings are wide enough to provide added strength to maintain a fracture reduction. Similar to the single layer design, for example, this multiple layer design features a pre-fabricated, mid-line, dorsal slit which is intended to give way for tissue expansion that occurs with post-traumatic swelling.

In an embodiment, the innermost and intermediate layers can be attached to each other, preferably sewn, or glued together, so that they can slide on the limb as one component. The outermost layer can then be placed over the limb and the packaging can then be removed. In an embodiment, the innermost, intermediate, and outermost layers can be attached together in the form of a single-unit sleeve. The single-unit sleeve can be removed from the packaging to remain soft and pliable while being slid over the limb. Alternately, the single-unit sleeve remains in the packaging to remain soft and pliable to confirm it is the proper size after being slid over the limb prior to removal of the packaging.

In an embodiment, an inner sleeve can be an absorbent fluid wicking which allows air and liquid to pass through. The intermediate layer can be a shock absorbing material, having a plurality of openings therein which allow air and liquid to pass through. The outer sleeve can be a protective material having a plurality of openings therein which allow air and liquid to pass through. Openings of the plurality of shock absorbing material openings are aligned to overlap openings of the plurality of the protective material openings in a manner so as to enable air and liquid to escape from the skin of the wearer.

The patient has a well fitted, soft cast and would only have to submerge his or her arm in a container of warm water for it to harden into a well fitting, aerated cast that can be molded in accordance with known procedures as the cast dries and hardens.

The disclosure will be further illustrated with reference to the following specific examples. It is understood that these examples are given by way of illustration and are not meant to limit the disclosure or the claims to follow.

As shown in FIG. 1, an outer sleeve 40 can be made in a form ready to be slid from a package 42 onto a patient's arm. The outer sleeve, suitably made of fiberglass for example, is arranged in a pattern which facilitates airflow through the layer, such as in a lattice 43 or lattice-like pattern as shown in FIG. 1. The pattern can be designed to include spaces large enough to let sufficient air and liquid pass back and forth to enable aeration of the cast materials, while remaining structurally robust. In an embodiment, the strips making up each leg of the lattice are of sufficient width and thickness to hold a reduction and withstand 6 weeks of wear and tear use. Suitable patterns in accordance with the present disclosure include any patterns which enable sufficient air and liquid pass back and forth to enable aeration of the cast materials, while remaining structurally robust to hold a reduction and withstand the required wear and tear use of a cast.

The fiberglass sleeve can have a longitudinal slit or a plurality of slits 44, preferably a dorsal slit, as shown in FIG. 1 which allows the sleeve to expand or to be propped open with spacers to accommodate for post-traumatic swelling. The connected sections 41 of the lattice pattern 43 can be cut after cast placement to allow for expansion due to swelling. The slit further facilitates easy removal of the cast when desired.

Figure 2:
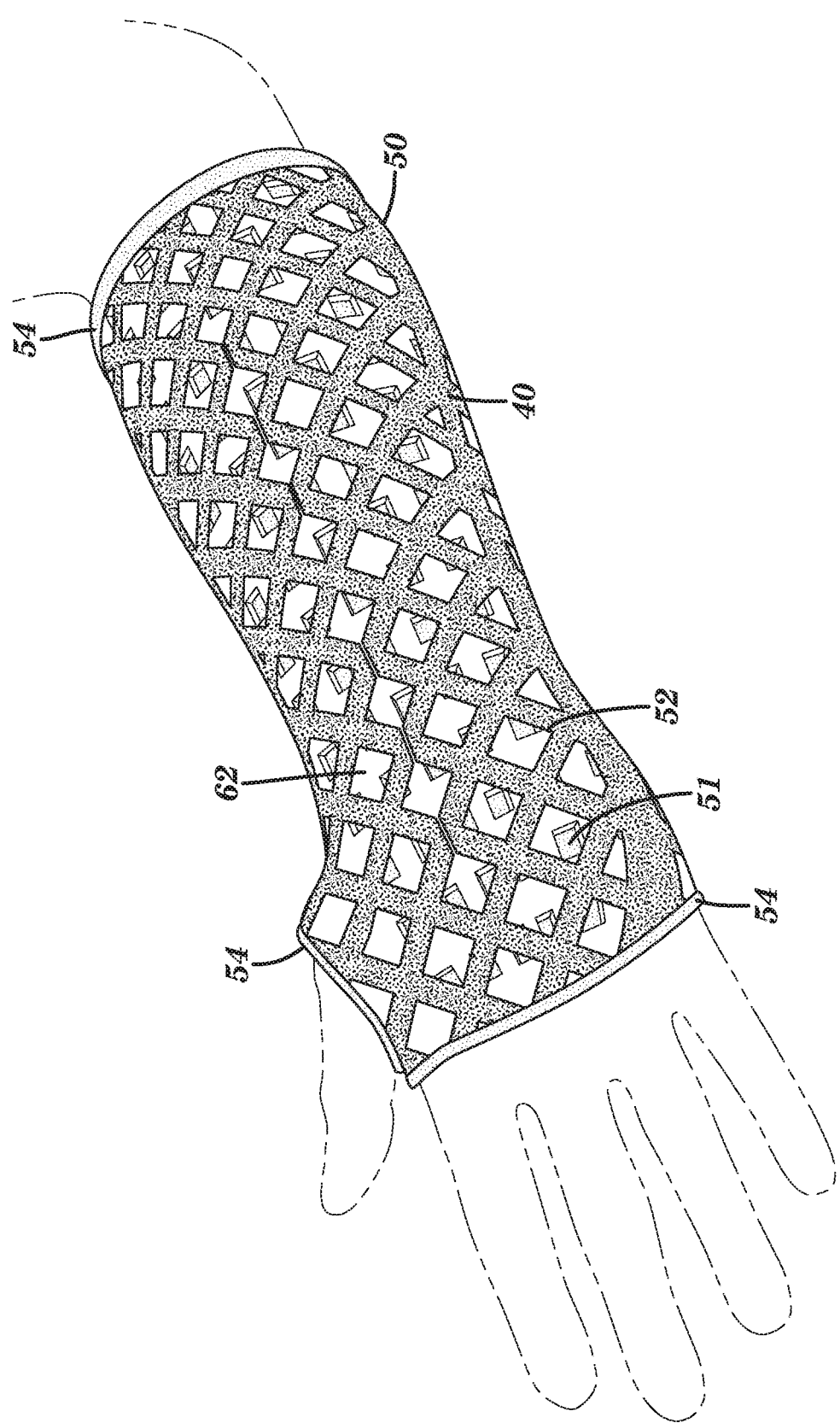
FIG. 2 is a drawing of an assembled cast of an embodiment of the of the present disclosure.

As shown in FIG. 2, a fitted cast 50 has holes 51 in an intermediate layer 62 aligned with holes 52 in the outer sleeve 40 which facilitate escape of moisture from the skin. The intermediate layer 62 provides cushioning which can be made of foam as well. The intermediate layer 62 can have a square grid-like formation 64, or resemble a lattice 43 in a repeating diamond-shaped formation as seen in the illustration of the outer sleeve 40, as shown in FIGS. 1-3.

Figure 3:
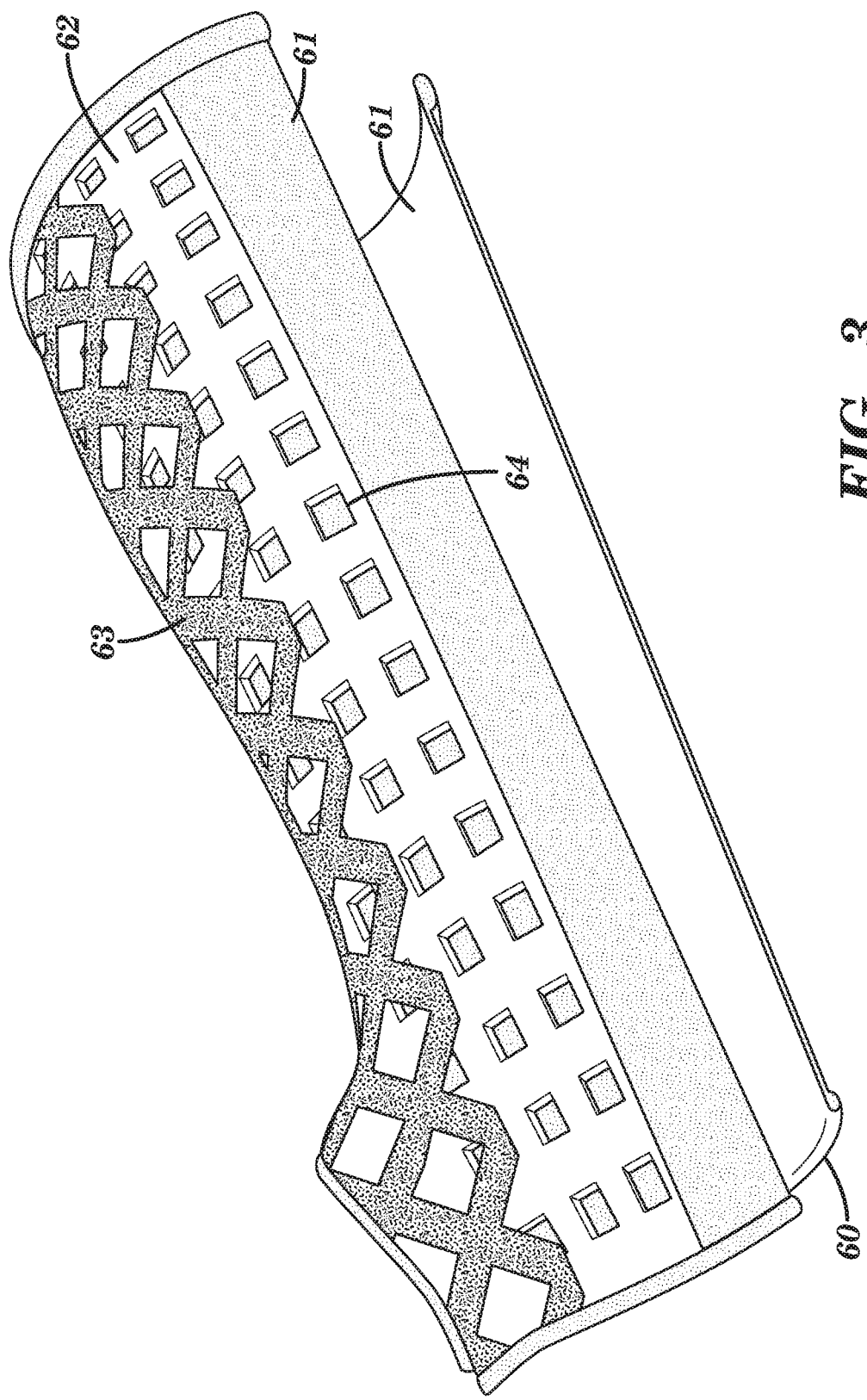
FIG. 3 is a drawing of a cut-away view of an embodiment of the cast of the present disclosure.

For example, as shown in FIG. 3, the intermediate layer 62 is depicted in a square grid format to facilitate liquid to pass between the cast layers. The edges of the intermediate layer 62, where the form makes contact with the palmar crease, the thumb, and the base of the forearm, can be elevated to form protective rings that are, for example, approximately 1 cm in width, and have thickness, for example, of ¾ to 1 cm greater than the rest of the sleeve. These and other dimensions can be provided to ensure that the edges of the outer sleeve do not dig into the patient's skin over the period of use. For example, as shown in FIG. 2, a raised cuff 54 from the foam layer protects the skin from being injured by the edges of the fiberglass layer.

FIG. 3 shows a cut-away view of an assembled cast, for example, from the innermost layer 61 of super absorbent wicking material, intermediate layer 62 of porous foam pad, and outer sleeve 63 of fiberglass lattice. The innermost layer 61 of the cast 60 can be composed of a porous, moisture wicking sleeve that when applied to the short arm extends from the palmar crease to approximately three finger breadths short of the cubital fossa, as shown in FIG. 2. This will allow the patient's skin to get wet over and over again, while protecting the skin from direct contact with the foam intermediate layer 62. In an embodiment, the innermost layer 61 is attached to the intermediate layer 62, such as by being sewn or glued, so that they form a single inner sleeve which can be applied in one step.

Figure 4:
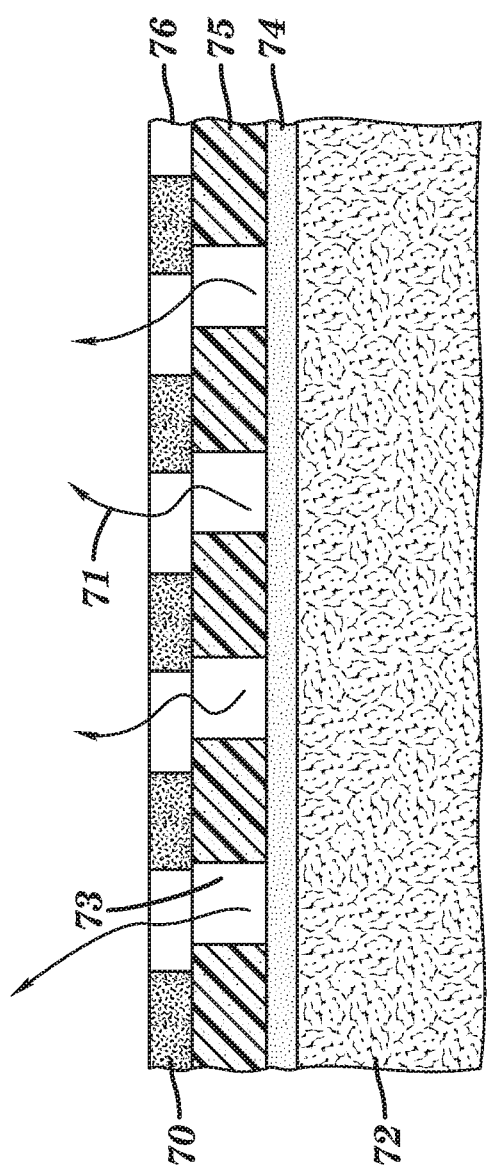
FIG. 4 is a drawing of a cross-sectional view of a portion of the cast of the present disclosure.

As shown in FIG. 4, the breathable cast 70 allows moisture 71 to escape from the skin 72 through the innermost layer 74 and overlapping holes 73 of the intermediate layer 75 and outer layer 76.

Figure 5:
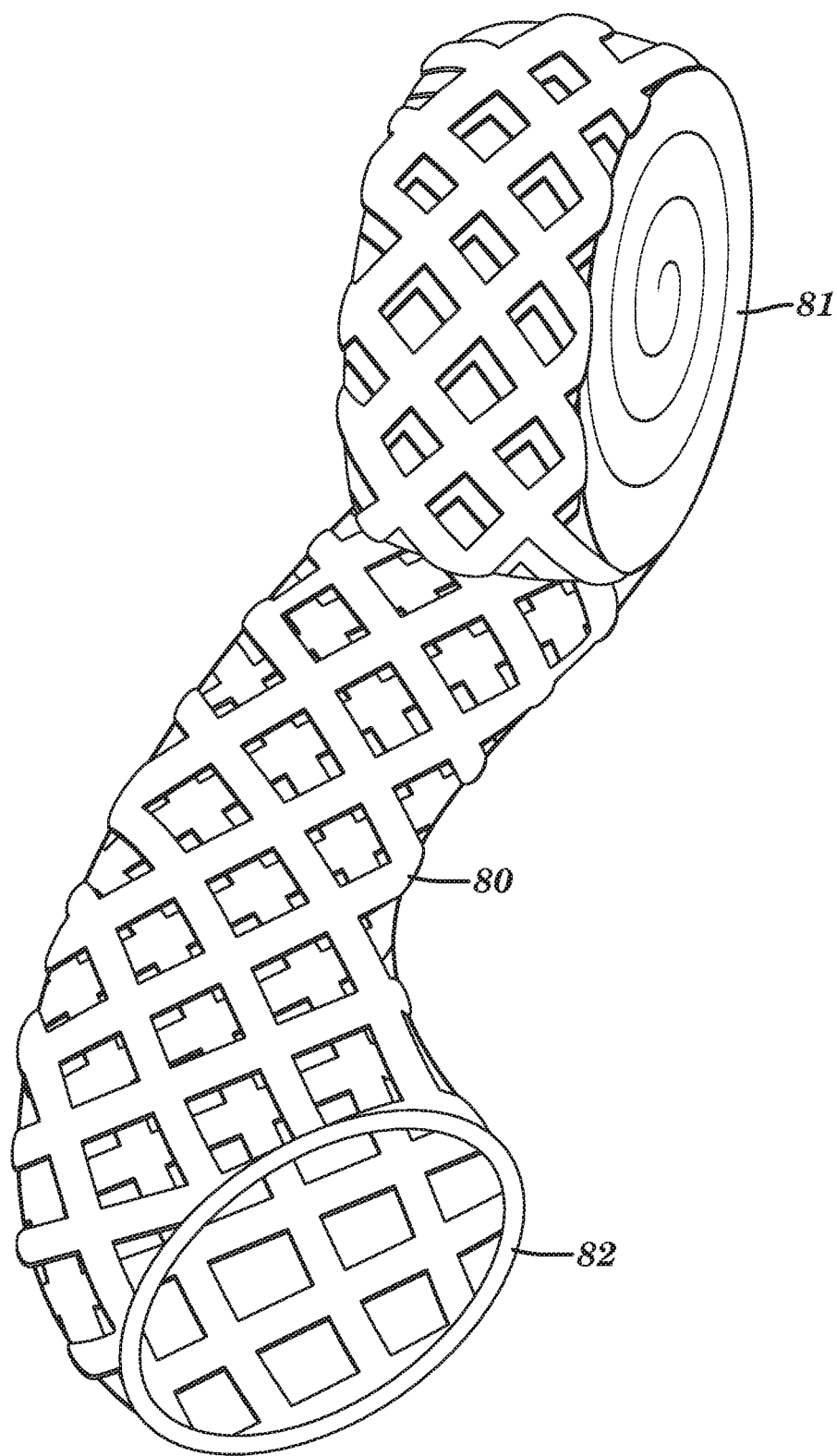
FIG. 5 is a drawing of an embodiment of the outer sleeve in the form of a roll of cylindrical netting of the present disclosure.

FIG. 5 is a drawing of an embodiment of the outer sleeve 80 in the form of a roll 81 of cylindrical netting 82. The single long sleeve 80 can be manufactured into cylindrical lattice-patterned cage or a knitted net in the desired lattice shape, for example, by use of a netting machine or cargo net knitting machine.

Figure 6:
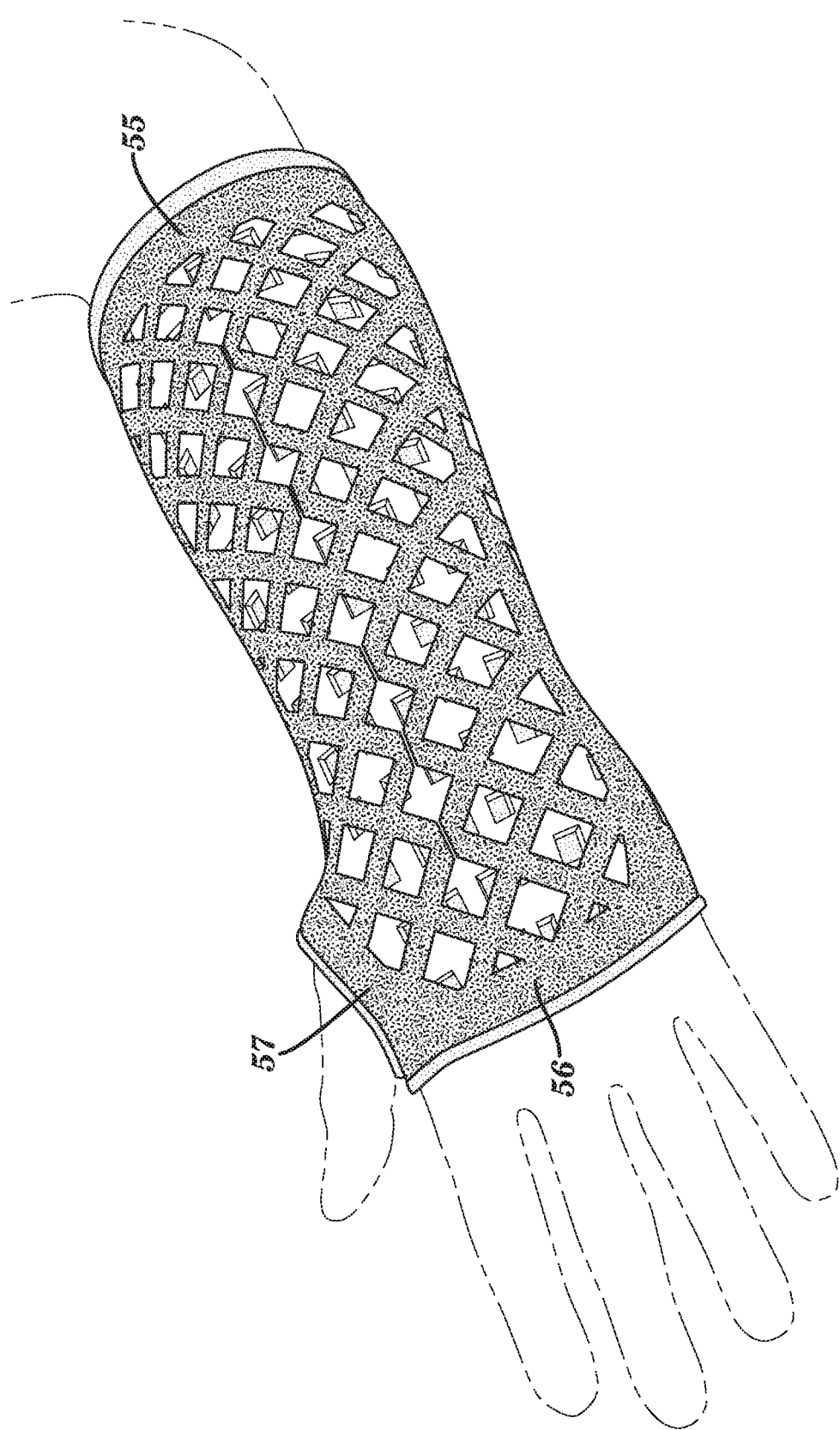
FIG. 6 is a drawing of a reinforced single layer outer sleeve of an embodiment of the present disclosure.

FIG. 6 is a drawing of a reinforced single layer outer sleeve of an embodiment showing a single layer sleeve cast provided with a solid ring on each end for added stability. The lattice pattern of a forearm sleeve terminates near the edge of the cast at the top 55, bottom 56, and around the thumb portion 57.

Figure 7:
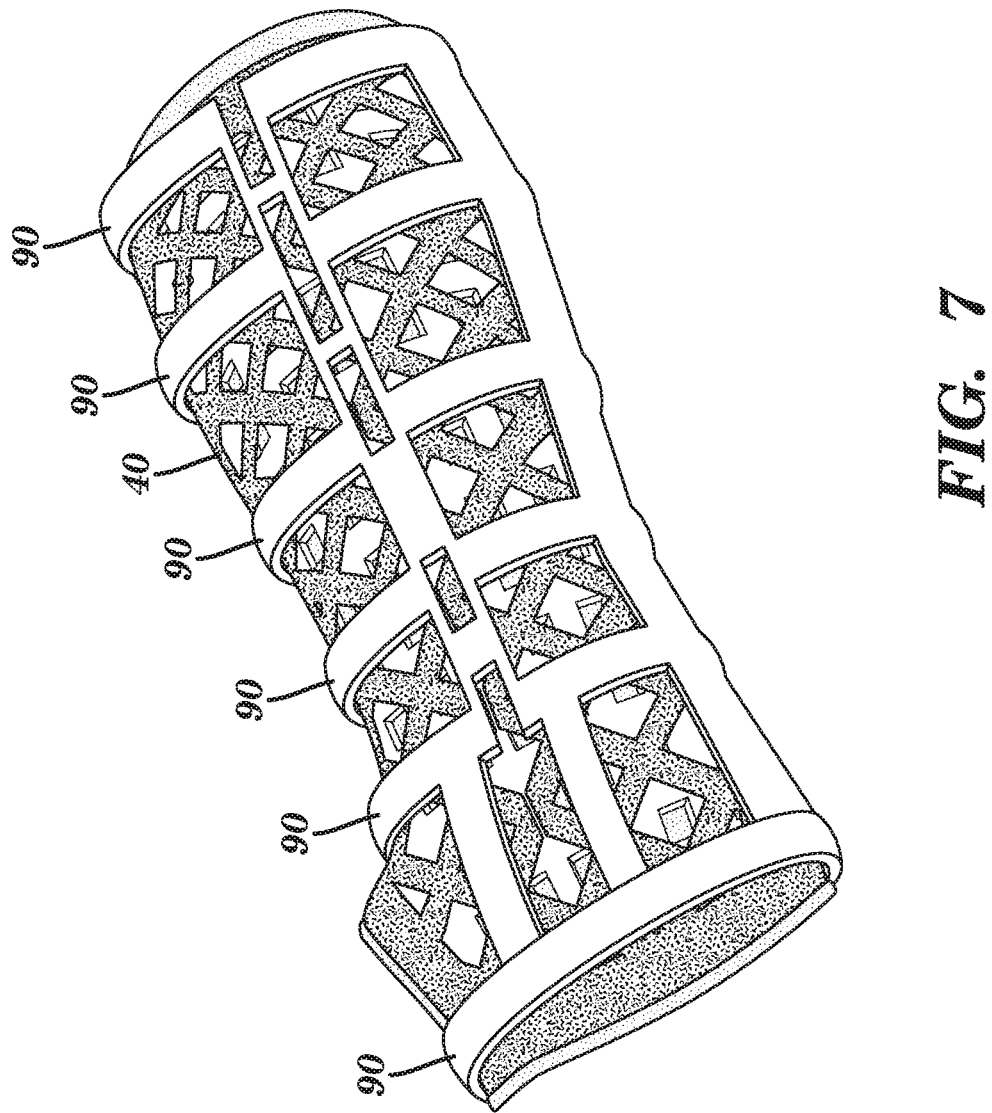
FIG. 7 is a drawing of a reinforced multiple layer outer sleeve of an embodiment of the present disclosure.

FIG. 7 is a drawing of a reinforced multiple layer outer sleeve 40 of an embodiment showing an added second outer layer composed of multiple spaced apart rings 90 provide strength to maintain a fracture reduction while promoting adequate air and water flow.

Casts and padding are successful when they are form fitting. Manufacturing the product by size based on bone length and/or height ensures that the device fits very well when slid into place. A survey of measurements in the population can be used to determine how many different stock sizes may be needed to generate an array of stock product sizes that is likely to accommodate the application to a majority of limbs. The stock sizes can be based on height, weight, and limb length. Once the first sleeve, such as the superabsorbent layer and foam combination is applied, the foam edges can be trimmed. This is followed by application of the stock sized outermost fiberglass layer.

As stated above, prior to cast formation the soft fiberglass can react with air and water and to avoid this is stored in such a way that it can be slid into place without removing the protective packaging. The packaging can be applied to the soft fiberglass in a manner so that the packaging is capable of being easily removed once the soft fiberglass sleeve is in place.

In accordance with an embodiment, the method for applying a cast to the patient includes applying an innermost layer over a limb by sliding a sleeve of innermost material over the limb, wherein the innermost layer is composed of a porous moisture wicking material. An intermediate layer is applied over the limb by sliding a sleeve of intermediate layer material over the limb, wherein the intermediate layer is composed of a shock-absorbing material having a plurality of holes therein. In an alternate embodiment, the innermost material and intermediate material can form a single inner sleeve and be applied together in a single step. While still in the packaging, an outermost sleeve in the form of a flexible tube, having a plurality of holes therein and a longitudinal slit is slid into place over the limb. The sleeve is fitted for size, removed from the packaging, and then trimmed if necessary. The soft material of the outer sleeve is exposed to water and air and allowed to air dry during the fitting process.

The cast of the present disclosure has several unique attributes. The form fitting nature of the cast enables the entire apparatus to be manufactured in different sizes. The use of hyper absorbent material, porous foam, and macro porous nature of all layers enables the cast to be breathable. The cast allows fluid and air to freely pass between the skin surface and the cast surface. Elimination of the need for a cast saw to remove the device is facilitated by the longitudinal slit. An ability to apply the cast without specialized training enables the cast to be utilized by emergency room staff, primary care staff, military medics, and rescue personnel. This allows emergency and urgent care physicians/nurses to definitively treat non-surgical fractures quickly and safely. Patients will have far fewer limitations with regard to exercise, hygiene and water activities. The pre-formed dorsal spilt will spare children from the often frightening, and occasionally painful experience of a cast saw. Removal can also be performed by clipping the lattice intersections rather than using a saw.

Other uses and variations of the present disclosure include use as a splint for wilderness expeditions. A few sizes for the leg or the arm could be carried by the medical staff for use in case there is a long bone fracture while the group is in a remote location.

Once the cost of the device becomes sufficiently low, it could be used in developing countries or for treatment of long bone fractures in the setting of disaster relief when shelter and clean, dry conditions are hard to come by and can pose significant logistical challenges.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A breathable cast comprising:
   an inner sleeve comprising an innermost layer comprising an absorbent fluid wicking material, which allows air and liquid to pass through, and an intermediate layer comprising a shock absorbing material, having a plurality of openings therein which allow air and liquid to pass through; and
   a hard outer sleeve comprising a cylindrical net at least four folded over layers thick comprising a plurality of openings therein which allow air and liquid to pass through, wherein the plurality of openings in the shock absorbing material overlap the plurality of openings in the outer sleeve in a manner so as to enable air and liquid to escape from the skin of the wearer, wherein the outer sleeve further comprises reinforcement rings.

2. A breathable cast comprising:
   an inner sleeve comprising an innermost layer comprising an absorbent fluid wicking material, which allows air and liquid to pass through, and an intermediate layer comprising a shock absorbing material, having a plurality of openings therein which allow air and liquid to pass through; and
   a hard outer sleeve comprising a cylindrical net comprising a plurality of openings therein which allow air and liquid to pass through, wherein the plurality of openings in the shock absorbing material overlap the plurality of openings in the outer sleeve in a manner so as to enable air and liquid to escape from the skin of the wearer, wherein the outer sleeve further comprises reinforcement rings.

3. The cast of claim 2, wherein the intermediate layer comprises foam, neoprene, or porous rubber.

4. The cast of claim 2, wherein the outer sleeve comprises a knitted fiberglass fabric impregnated with a water/air activated resin.

5. The cast of claim 2, wherein the outer sleeve comprises a longitudinal slit or a plurality of longitudinal slits from one end to the other end.

6. The cast of claim 2, wherein the outer sleeve comprises a repeating diamond shaped lattice design.

7. The cast of claim 2, wherein the cast comprises an upper extremity, lower extremity, long arm, short arm, short leg, long leg, dorsal hood, or hip spica cast.

8. The cast of claim 2, wherein the innermost layer and the intermediate layer form a single layer.

9. The cast of claim 2, wherein the innermost layer and the intermediate layer form separate layers.

10. A method for applying a breathable cast to a patient comprising:
    applying an inner sleeve comprising an innermost layer and an intermediate layer over a limb of the patient by sliding the inner sleeve over the limb, wherein the innermost layer is comprised of an absorbent fluid wicking material, which allows air and liquid to pass through, and the intermediate layer is comprised of a shock absorbing material, having a plurality of openings therein which allow air and liquid to pass through;
    applying a pliable outer sleeve cylindrical net, comprising a knitted fiberglass fabric impregnated with a water/air activated resin comprising a plurality of openings therein which allow air and liquid to pass through, into place over the inner sleeve by folding the outer sleeve back over itself at least 3 times, wherein the plurality of openings in the shock absorbing material overlap the plurality of openings in the outer sleeve in a manner so as to enable air and liquid to escape from the skin of the patient; and
    fitting the cast to the patient while allowing the cast to air dry during the fitting thereof or thereafter activating the resin with water to harden the outer sleeve, wherein the outer sleeve further comprises reinforcement rings.

11. A method for applying a breathable cast to a patient comprising:
    applying an inner sleeve comprising an innermost layer and an intermediate layer over a limb of the patient by sliding the inner sleeve over the limb, wherein the innermost layer is comprised of an absorbent fluid wicking material, which allows air and liquid to pass through, and the intermediate layer is comprised of a shock absorbing material, having a plurality of openings therein which allow air and liquid to pass through;
    applying a pliable outer sleeve cylindrical net, comprising a knitted fiberglass fabric impregnated with a water/air activated resin comprising a plurality of openings therein which allow air and liquid to pass through, into place over the inner sleeve, wherein the plurality of openings in the shock absorbing material overlap the plurality of openings in the outer sleeve in a manner so as to enable air and liquid to escape from the skin of the patient; and
    fitting the cast to the patient while allowing the cast to air dry during the fitting thereof or thereafter activating the resin with water to harden the outer sleeve, wherein the outer sleeve further comprises reinforcement rings.

12. The method of claim 11, wherein the outer sleeve is applied over the limb while still in protective packaging.

13. The method of claim 11, wherein the outer sleeve is removed from protective packaging prior to being applied over the limb.

14. The method of claim 11, wherein the outer sleeve comprises a pre-sized sleeve to fit the limb.

15. The method of claim 11, wherein the innermost and intermediate layers are attached to each other prior to the application over the limb.

16. The method of claim 11, wherein the outer sleeve is attached to the innermost and intermediate layers prior to the application over the limb.

17. The method of claim 11, wherein the intermediate layer comprises foam, neoprene, or porous rubber.

18. The method of claim 11, wherein the outer sleeve comprises a longitudinal slit or a plurality of longitudinal slits from one end to the other end.

19. The method of claim 11, wherein the outer sleeve is made by use of a netting machine or cargo net knitting machine.

* * * * *